United States Patent [19]
Nakatsu et al.

[11] Patent Number: 5,965,518
[45] Date of Patent: Oct. 12, 1999

[54] FRAGRANCE COMPOSITIONS HAVING ANTIMICROBIAL ACTIVITY

[76] Inventors: Tetsuo Nakatsu, Chappaqua; Augustinus G. Van Loveren, Bedford, both of N.Y.; Raphael K. L. Kang, Northvale; Alba T. Cilia, River Edge, both of N.J.

[21] Appl. No.: 09/027,981

[22] Filed: Feb. 23, 1998

[51] Int. Cl.⁶ .............................. A61K 7/46; A61K 7/00; A61K 7/42; A61K 7/32
[52] U.S. Cl. .................................. 512/1; 424/47; 424/59; 424/65; 424/76.1; 424/401; 424/404; 512/5; 512/20; 512/26
[58] Field of Search ............................. 512/1, 5, 20, 26; 424/401, 404, 47, 59, 65, 76.1

[56] References Cited

U.S. PATENT DOCUMENTS 5,482,635  1/1996  Behan et al. .............................. 252/8.6
5,658,584  8/1997  Yamaguchi .............................. 424/405

OTHER PUBLICATIONS

Pending Application No. 08/995,261 of Tetsuo Nakatsu et al. "Antimicrobial Composition," filed Dec. 19. 1997, p. 2 line 13 and p. 5 line 19.

*Primary Examiner*—Shelley A. Dodson
*Assistant Examiner*—Marina Lamm

[57] ABSTRACT

A fragrance composition having antimicrobial activity comprises between 3 and 20% phenolic compounds, and between 20 and 80% non-aromatic terpenoids. The fragrance composition may also, either alternatively or additionally, include essential oils containing phenolic compounds as a major constituent, and/or essential oils containing non-aromatic terpenoids as a major constituent. The fragrance composition further has an Odor Intensity Index of less than 100, and an Odor Evaluation Acceptability Index of greater than 50. The fragrance composition is suitable for use in a variety of products.

18 Claims, No Drawings

FRAGRANCE COMPOSITIONS HAVING ANTIMICROBIAL ACTIVITY

BACKGROUND OF THE INVENTION

The present invention relates to fragrance compositions exhibiting antimicrobial activity with a hedonically acceptable odor. The present invention also relates to formulations incorporating such fragrance compositions.

Fragrances are commonly incorporated in a wide variety of household and industrial items, from perfumes to cleansers, to impart a pleasing odor to the item. Some fragrances have been reported to have weak bacteriostatic activity. However, this activity is believed to be too weak to be of practical use. See J. A. Morris et al., J. Amer. Oil Chem. Soc. 56(5):595–603 (1979), the entirety of which is herein incorporated by reference. To overcome this weak activity and achieve antimicrobial fragrances of practical use, either as bacteriostatic agents in preservatives and the like or as bactericidal agents in sanitizers & disinfectants and the like, combinations of fragrance materials with other materials are employed. For example, fragrances have been combined with a cationic phospholipid (U.S. Pat. No. 5,420,104). Fragrances have also been combined with a preservative and surface active agent (U.S. Pat. No. 5,306,707) or with an organic acid (European Patent Application 0 570 794 A2).

Another possible way to achieve useful activity is to increase the effective fragrance ingredient concentration until the desired activity is achieved (e.g. U.S. Pat. No. 5,306,707, wherein 30% effective perfume ingredients are needed to achieve activity in the combination). However, this produces an active perfume having an odor that is not pleasing and is not acceptable to the consumer in a final consumer product. Further, these fragrances also have an unacceptability high odor intensity index as the perfumer tries to cover the odor of the effective material with large amounts of other fragrance ingredients or materials having a high intensity. There is an inverse relationship of activity of the effective fragrance material and odor acceptability; that is, as antimicrobial activity increases, odor acceptability decreases.

OBJECTS AND SUMMARY OF THE INVENTION

It is an object of the present invention to overcome the limitations of the prior art.

It is another object of the present invention to provide a fragrance composition which is both acceptable to consumers and exhibits antimicrobial activity.

It is another object of the present invention to provide a cleaning composition containing a fragrance which is both acceptable to consumers and exhibits antimicrobial activity.

We have discovered a way to create fragrances with sufficient antimicrobial activity to be useful and yet have an good odor acceptability. After extensive research, we have discovered that using a combination of between 3 and 20% of phenolic compounds, such as thymol, and between 20 and 80% of non-aromatic terpenoids, such as Terpinolene 20, produces useful antimicrobial activity. Further, at these levels, a good odor acceptability and useful intensity fragrance can also be achieved. Essential oils containing phenolic compounds as the major constituent, and essential oils containing non-aromatic compounds as the major constituent may also be used.

Briefly stated, a fragrance composition having antimicrobial activity comprises between 3 and 20% phenolic compounds, and between 20 and 80% non-aromatic terpenoids. The fragrance composition may also, either alternatively or additionally, include essential oils containing phenolic compounds as a major constituent, and/or essential oils containing non-aromatic terpenoids as a major constituent. The fragrance composition further has an Odor Intensity Index of between 110 and 130, and an Odor Evaluation Acceptability Index of greater than 50. The fragrance composition is suitable for use in a variety of products.

According to an embodiment of the present invention, a fragrance composition having antimicrobial activity comprises between 3 and 20% f a phenolic compound, and between 20 and 80% of a non-aromatic terpenoid, wherein the fragrance composition has an Odor Intensity Index of between 110 and 130, and the fragrance composition has an Odor Evaluation Acceptability Index of greater than 50, and the fragrance composition satisfies at least two of the following four criteria a: The fragrance achieves a Minimal Inhibitory Concentration (MIC) in media at or below normal use concentration within two days;
  b: The fragrance reduces the microbial number by at least 1.5 log cfu/ml within 30 minutes, preferably within 5 minutes, at ambient temperature at or below normal use concentration;
  c: The fragrance in the appropriate product at normal use concentration reduces the microbial number by at least 1.5 log cfu/ml within 30 minutes, preferably within 5 minutes, at product use temperature;
  d: The fragrance in the appropriate product used at an appropriate dilution reduces or inhibits microbial growth as tested by generally accepted methods published or recommended by any of the following bodies—Association of Official Analytical Chemists, American Society for Testing and Materials, American Assoc. of Textile Chemists and Colorists, American Public Health Association, United States Food and Drug Administration, United States Environmental Protection Agency, European Committee for Standardization, United States Pharmacopoeia, and Cosmetic, Toiletry, and Fragrance Association.

As used in this application, "normal use concentration" refers to a concentration that produces a fragrance having a hedonistically acceptable odor. "Product use temperature" refers to a temperature within a range in which the product is usually used by consumers.

The above, and other objects, features and advantages of the present invention will become apparent from the following description.

DETAILED DESCRIPTION OF THE PREFERRED EMBODIMENT

The fragrances that exhibit antimicrobial effects according to the present invention are those that satisfy the following criteria:

1. the fragrances contain between 3 and 20% phenolic compounds, and between 20 and 80% non-aromatic terpenoids,
2. The fragrance has an Odor Intensity Index of between 110 and 130, and
3. the fragrance has an Odor Evaluation Acceptability Index of greater than 50, and
4. the fragrance satisfies at least two of the following four criteria
   a: The fragrance achieves a Minimal Inhibitory Concentration (MIC) in media at or below normal use concentration within two days;

b: The fragrance reduces the microbial number by at least 1.5 log cfu/ml within 30 minutes, preferably 5 minutes, at ambient temperature at or below normal use concentration;

c: The fragrance in the appropriate product at normal use concentration reduces the microbial number by at least 1.5 log cfu/ml within 30 minutes, preferably 5 minutes at product use temperature;

d: The fragrance in the appropriate product used at an appropriate dilution reduces or inhibits microbial growth as tested by generally accepted methods published or recommended by any of the following bodies:

AOAC: Association of Official Analytical Chemists
ASTM: American Society for Testing and Materials
AATCC: American Assoc. of Textile Chemists and Colorists
APHA: American Public Health Association
FDA: United States Food and Drug Administration
EPA: United States Environmental Protection Agency
CEN: European Committee for Standardization
USP: United States Pharmacopoeia
CTFA: Cosmetic, Toiletry, and Fragrance Association.

Fragrances, as used in this application, are made by selecting and combining materials published in Allured Flavor and Fragrance Materials (Allured Publishing Co., Carol Stream, Ill., 1997 ed.). These compounds include various esters, aldehydes, alcohols, ketones, terpinenes, ethers, acetals, nitrites, essential oils, heterocyclic nitrogen-containing compounds or sulfur-containing compounds. Examples of phenolic fragrances appropriate for use in the present invention include amyl salicylate, cavacrol, dihydroeugenol, eugenol, hexyl eugenol, hexyl salicylate, isoeugenol, methyl eugenol, methyl isoeugenol, methyl salicylate, tert butyl cresol, thymol, and vanillin. Examples of non-aromatic terpenoid compounds include cedrene, cineole, citral, citronellal, citronellol, cymene, paradihydrolinalool, dihydromyrcenol (DH myrcenol), farnesol, geraniol, hexyl cinnamaldehyde, hydroxycitronallol, hydroxycitronellal, isocitral, limonene, linalool, longifolene, menthol, nerol, nerolidiol, phellendrene, terpinene, terpinenol, and tetrahydromyrcenol (TH myrcenol).

The phenolic compounds and non-aromatic terpenoids may be added in an isolated form. Alternatively or additionally, essential oils containing the phenolic compounds and/or the non-aromatic terpenoids as major constituents may be added, with the final concentrations of the phenolic compounds and the non-aromatic terpenoids being within the range of the invention. The term "major constituent" refers to those essential oils having phenolic compounds or non-aromatic terpenoids, wherein the phenolic compounds or non-aromatic terpenoids constitute more than 50% by weight of the composition of the essential oil. It is well-known in the art that such essential oils may also contain lesser amounts of the other constituent, i.e., essential oils containing phenolic compounds often contain lesser amounts of non-aromatic compounds, and essential oils containing non-aromatic compounds often contain lesser amounts of phenolic compounds. Essential oils including phenolic compounds as the major constituent include, for example, anise oil, bay oil terpineless, clove bud, clove leaf, clove oil, clove stem, origanum oil, Peru balsam, pimento oil, and thyme oil. Essential oils including non-aromatic terpenoids as the major constituent include, for example, buchu oil, caraway oil, carrot seed, cedar leaf, citronella oil, citrus oil, copaiba oil, geranium oil, gergamot, lavender oil, mint oil, orange oil, parsley oil, patchouly oil, pine oil, rosemary oil, sage oil, tagette oil, and ylang ylang.

The fragrances should have a high enough Odor Intensity Index to be usable at low doses in consumer products. The fragrances preferably have an intensity comparable to that of 50% benzyl acetate, that is, an Odor Intensity Index between 110 and 130. The fragrances also preferably have an Odor Evaluation Acceptability Index of greater than 60, in order to be acceptable to consumers. More preferably, the Odor Evaluation Acceptability Index is greater than 65.

Various fragrances were tested for antimicrobial activity. The effectiveness of the various fragrances was determined with reference to the above four criteria. AMPAT-A is a fresh aldehydic light spicy fragrance with a natural lemon accord. AMPAT-B has a green aldehydic citrus accord with a woody floral background. AMPAT-C is a spicy floral and lavandacious fragrance with a fresh agrumen accord. AMPAT-D has a aldehydic citrus floral and warm powdery woody fragrance. AMPAT-E has an herbal floral fragrance. The compositions of the various fragrances are shown in Tables 1–5.

TABLE 1

Components of AMPAT-A

| Component | Wt. Percent |
|---|---|
| Citral | 4.0 |
| Citronellyl nitrile 1* | 1.5 |
| Clove leaf oil | 5.0 |
| Citrustone 1* | 14.05 |
| Geraniol | 6.0 |
| Grapefruit oil terpenes | 6.0 |
| Lime oil terpenes | 3.25 |
| Linalool | 7.7 |
| Orange oil terpenes white | 19.0 |
| Suzaral* | 1.0 |
| Terpinolene 20 | 20.0 |
| TH Mycenol | 5.0 |
| Thymol | 7.5 |

*Available from Takasago International Corp.

TABLE 2

Components of AMPAT-B

| Component | Wt. Percent |
|---|---|
| Eugenol | 3.9 |
| Thymol | 8.6 |
| DH Myrcenol | 15.1 |
| Marine note A | 11.35 |
| Citral | 1.6 |
| Geraniol pure | 8.6 |
| Grapefruit oil terpenes | 11.5 |
| Cedarwood oil texas white | 7.8 |
| Linalool | 0.8 |
| Clove leaf oil | 0.8 |
| Terpinolene 20 | 9.4 |
| TH Myrcenol | 3.9 |
| Musk T* | 0.7 |
| Bergamot sub G1 berg | 12.0 |
| Suzaral* | 1.9 |
| Oranta, L, super* | 0.15 |
| Lavandin grosso | 1.9 |

*Available from Takasago International Corp.

TABLE 3

Components of AMPAT-C

| Component | Wt. Percent |
| --- | --- |
| Amyl salisylate | 1.5 |
| Bergamot sub G1 berg | 4.0 |
| Cedarwood oil texas white | 1.5 |
| Cinnaldehyde | 3.0 |
| Clove leaf oil | 6.5 |
| DH Myrcenol | 15.0 |
| Geraniol intermediate 60 | 3.0 |
| Herbal tone F | 9.6 |
| Hexyl cinnamaldehyde | 3.5 |
| Hexyl salisylate | 9.0 |
| Lavandin grosso | 2.0 |
| Muguet sub G1 mugu | 3.5 |
| Olibanum re "T" @ 50% DPG | 1.5 |
| Orange oil pera brazil | 5.0 |
| Patchouly oil deironized | 1.25 |
| Phellandrene, alpha | 1.65 |
| Terpinolene 20 | 7.0 |
| Thymol | 10.0 |
| Verdox | 1.5 |
| Vertenex | 10.0 |

TABLE 4

Components of AMPAT-D

| Component | Wt Percent |
| --- | --- |
| Benzyl acetate | 2.0 |
| Benzyl benzoate | 7.0 |
| Hedione | 1.2 |
| Herboxane | 0.15 |
| Indolal @ 10% DPG | 0.2 |
| Kovanol | 2.5 |
| Lanvander base CH5 | 6.95 |
| Lemon oil california | 2.0 |
| Lilial | 0.5 |
| Methyl napth ketone @ 10% DPG | 0.5 |
| Petitgrain oil | 0.75 |
| Rose sub CH5 | 5.095 |
| Sweet musk base CH5 | 48.75 |
| Woody base CH5 | 19.905 |
| Ylang oil #3 | 0.75 |
| Ylang sub G1 Ylan | 1.75 |

TABLE 5

Components of AMPAT-E

| Component | Wt. Percent |
| --- | --- |
| Thymol | 10 |
| Terpinolene 20 | 7 |
| DH Myrcenol | 10 |
| Vertenex | 10 |
| Dipropylene glycol | 63 |

Experiment 1

For determination of the antimicrobial activity criterion a above, fragrances were dissolved in an equal volume of dimethylformamide, then serially diluted. Aliquots (30 µl) were added to enriched nutrient broth (3 ml), followed by 60 µl of an overnight culture of the test microorganism. The cultures were incubated at 30° C. for 2 days. Growth was determined as an increase in turbidity at 660 nm. The results are shown in Table 6. MIC refers to the Minimal Inhibitory Concentration, and is the lowest concentration of the fragrance which completely inhibits growth. ATCC refers to the American Type Culture Collection (Rockville, Md.).

TABLE 6

| Fragrance | E. coli ATCC 11229 MIC | S. aureus ATCC 6538 MIC | S. epidermidis ATCC 12228 MIC |
| --- | --- | --- | --- |
| AMPAT-A | 0.25% | 0.063% | 0.031% |
| AMPAT-B | 0.25% | 0.031% | 0.031% |
| AMPAT-C | ~0.5%* | 0.031% | 0.063% |
| AMPAT-D | >0.5% | >0.25% | >0.25% |
| AMPAT-E | 0.25% | 0.063% | 0.125% |

*activity between 50% and 80% inhibition

Referring to Table 6, it can be seen that AMPAT-A, -B, -C, and -E all exhibited strong antimicrobial activity against *Staphylococcus aureus* ATCC 6538 and *Staphylococcus epidermidis* ATCC 12228, while AMPAT-D did not. Further, it can be seen that AMPAT-A, -B, -E, and to a lesser extent -C all exhibited antimicrobial activity against *E. coil* ATCC 11229, while AMPAT-D did not.

For determination of the antimicrobial activity criteria b and c above, the test fragrances were diluted in dimethylformamide. Microorganisms (*E. coli* ATCC 11229) were grown in an enriched nutrient broth and sampled to determine the bacterial number. The test fragrances were inoculated into this solution, mixed using a Vortex mixer and incubated. Samples were removed at 1 and 5 minutes and diluted into D/E Neutralization broth (Difco, Detroit, Mich., USA). The treated samples were then plated onto solid media and incubated at 37° C. for 24 hours. Colony-forming units were then counted and normalized as cfu/ml. The results with respect to antimicrobial activity criterion b above are shown in Table 7.

TABLE 7

| | Concentration (wt %) | Log reduction (1 min) | Log reduction (5 min) |
| --- | --- | --- | --- |
| AMPAT-A | 0.25 | 1.3 | 3.2 |
| AMPAT-B | 0.25 | 0.6 | 1.6 |
| AMPAT-C | 0.25 | 0.9 | 2.6 |
| AMPAT-D | 0.25 | 0.2 | 0.2 |
| AMPAT-E | 0.25 | 0.6 | 1.5 |

Referring to Table 7, it can be seen that fragrances AMPAT-A, -B, -C and -E each reduce the microbial number by at least 1.5 log cfu/ml within 5 minutes at ambient temperature at or below normal use concentration. AMPAT-D did not significantly reduce the microbial number after 5 minutes of exposure to the test microorganisms.

The results with respect to antimicrobial activity criterion c are shown in Table 8. In this test, the fragrances were tested in a nonionic surfactant cleaner formulation having a pH above 7.

TABLE 8

| | Concentration (wt %) | Dilution | Log reduction (5 min) |
| --- | --- | --- | --- |
| control | — | 1:4 | 1 |
| AMPAT-A | 1% | 1:4 | >4 |
| AMPAT-B | 1% | 1:4 | >4 |
| AMPAT-C | 1% | 1:4 | >4 |
| AMPAT-D | 1% | 1:4 | 1.3 |
| AMPAT-E | 1% | 1:4 | >4 |

It can be seen that fragrances AMPAT-A, -B, and -C, in the appropriate product at normal use concentration each reduced the microbial number by at least 1.5 log cfu/ml within 5 minutes at product use temperature. However, AMPAT-D did not reduce the microbial number by at least 1.5 log cfu/ml within 5 minutes at product use temperature.

A summary of the tested fragrances and the results are shown in Table 9. A "✓" sign indicates that the fragrance satisfied the criteria, while a "−" sign indicates that the fragrance did not satisfy the criteria.

TABLE 9

| Fragrance | Test Criteria | | | |
|---|---|---|---|---|
| | a | b | c | d |
| AMPAT-A | ✓ | ✓ | ✓ | ✓ |
| AMPAT-B | ✓ | ✓ | ✓ | ✓ |
| AMPAT-C | ✓ | ✓ | ✓ | ✓ |
| AMPAT-D | − | − | − | − |
| AMPAT-E | ✓ | ✓ | ✓ | ✓ |

Experiment 2

The various fragrances were all tested for Odor Intensity Index and Odor Evaluation Acceptability Index. For evaluation of the odor acceptability, each fragrance was incorporated into a cleanser base and evaluated by a panel of at least 20 persons. The cleanser base was a nonionic surfactant composition containing 1% of each fragrance. Individual assessment scores on a scale of 1–5 were normalized and averaged as described in U.S. Pat. No. 5,501,805, the entirety of which is herein incorporated by reference. The normalized and averaged Odor Evaluation Acceptability Index values are shown in Table 10.

TABLE 10

| Fragrance | Odor Evaluation Acceptability Index |
|---|---|
| AMPAT-A | 78 |
| AMPAT-B | 76 |
| AMPAT-C | 65 |
| AMPAT-D | 69 |
| AMPAT-E | 46 |

Referring to Table 10, it can be seen that all of the fragrances had Odor Evaluation Acceptability Index values above 50, except AMPAT-E. Furthermore, all the fragrances, except AMPAT-E, had values that were in the preferred range, that is, above 65.

The Odor Intensity Index values were produced by comparing the odor intensity of each fragrance oil relative to benzyl acetate at various dilutions (see U.S. Pat. No. 5,501,805). An panel of at least four persons evaluated the odor intensity of each fragrance relative to the standards, which were each assigned an Odor Intensity Index value for reference. The individual assessment scores were normalized and averaged to provide a consensus Odor Intensity Index value for each sample. The results are shown in Table 11.

TABLE 11

| Test Compound | Odor Intensity Index |
|---|---|
| AMPAT-A | 118 |
| AMPAT-B | 122 |
| AMPAT-C | 125 |
| AMPAT-D | 127 |
| AMPAT-E | 116 |
| 10% Benzyl Acetate | 102 |
| 20% Benzyl Acetate | 108 |

TABLE 11-continued

| Test Compound | Odor Intensity Index |
|---|---|
| 50% Benzyl Acetate | 120 |
| Neat Benzyl Acetate | 132 |

Referring to Table 11, it can be seen that all the fragrances had Odor Intensity Index values in the range about 50% benzyl acetate, that is, between 110 and 130. However, as noted above, AMPAT-E did not satisfy the Odor Evaluation Acceptability Index requirement, and AMPAT-D did not satisfy the antimicrobial activity requirements. Therefore, these fragrances are not included in the scope of the present invention. A summary of the fragrances tested and the results of those tests are shown in Table 12.

TABLE 12

| Fragrance | Odor Intensity Index | Odor Evaluation Acceptability Index | Antimicrobial Activity |
|---|---|---|---|
| AMPAT-A | ✓ | ✓ | ✓ |
| AMPAT-B | ✓ | ✓ | ✓ |
| AMPAT-C | ✓ | ✓ | ✓ |
| AMPAT-D | ✓ | ✓ | − |
| AMPAT-E | ✓ | − | ✓ |

Having described preferred embodiments of the invention, it is to be understood that the invention is not limited to those precise embodiments, and that various changes and modifications may be effected therein by one skilled in the art without departing from the scope or spirit of the invention as defined in the appended claims.

What is claimed is:

1. A fragrance composition having antimicrobial activity, comprising:

between 3 and 20% of a phenolic compound; and between 20 and 80% of a non-aromatic terpinoid;

wherein said fragrance composition has an Odor Intensity Index of between 110 and 130, and said fragrance composition has an Odor Evaluation Acceptability Index of greater than 50, and said fragrance composition satisfies at least two of the following four criteria a: said fragrance composition achieves a Minimal Inhibitory Concentration (MIC) in media at or below normal use concentration within two days;

b: said fragrance composition reduces the microbial number by at least 1.5 log cfu/ml within 30 minutes at ambient temperature at or below normal use concentration;

c: said fragrance composition at normal use concentration reduces the microbial number by at least 1.5 log cfu/ml within 30 minutes at product use temperature;

d: said fragrance composition at normal use concentration reduces or inhibits microbial growth.

2. A fragrance composition according to claim 1, wherein said fragrance composition has an Odor Evaluation Acceptability Index of greater than 65.

3. A fragrance composition according to claim 1, wherein said fragrance composition is a member selected from the group consisting of AMPAT-A, AMPAT-B, and AMPAT-C, wherein:

AMPAT-A is a composition containing 4.0 wt. percent citral, 1.5 wt. percent citronellyl nitrile 1, 5.0 wt. percent clove leaf oil, 14.05 wt. percent citrustone 1, 6.0 wt. percent geraniol 6.0 wt. percent grapefruit oil terpenes, 3.25 wt. percent lime oil terpenes, 7.7 wt.

percent linalool 19.0 wt. percent orange oil terpenes white, 1.0 wt. percent suzaral, 20.0 wt. percent terpinolene 20, 5.0 wt. percent TH myrcenol, and 7.5 wt. percent thymol;

AMPAT-B is a composition containing 3.9 wt. percent eugenol, 8.6 wt. percent thymol, 15.1 wt. percent DH myrcenol, 11.35 wt. percent marine note A, 1.6 wt. percent citral, 8.6 wt. percent geraniol pure, 11.5 wt. percent grapefruit oil terpenes, 7.8 wt. percent cedarwood oil texas white, 0.8 wt. percent linalool, 0.8 wt. percent clove leaf oil, 9.4 wt. percent terpinolene 20, 3.9 wt. percent TH myrcenol, 0.7 wt. percent musk T, 12.0 wt. percent bergamot sub GL berg, 1.9 wt. percent suzaral, 0.15 wt. percent oranta, L, super, and 1.9 wt. percent lavandin grosso;

AMPAT-C is a composition containing 1.5 wt. percent amyl salisylate 4.0 wt. percent bergamot sub GL berg, 1.5 wt. percent cedarwood oil texas white, 3.0 wt. percent cinnaldehyde, 6.5 wt. percent clove leaf oil, 15.0 wt. percent DH myrcenol, 3.0 wt. percent geraniol intermediate 60, 9.6 wt. percent herbal tone F, 3.5 wt. percent hexyl cinnamaldehyde, 9.0 wt. percent hexyl salisylate, 2.0 wt. percent lavandin grosso, 3.5 wt. percent muguet sub GL mugu, 1.5 wt. percent olibanum re "T" @ 50% DPG, 5.0 wt. percent orange oil pera brazil, 1.25 wt. percent patchouly oil deironized, 1.65 wt. percent phellandrene, alpha, 7.0 wt. percent terpinolene 20, 10.0 wt. percent thymol, 1.5 wt. percent verdox, and 10.0 wt. percent vertenex.

4. A fragrance composition according to claim 1, wherein said phenolic compound is at least one of amyl salicylate, carvacrol, dihydroeugenol, eugenol, hexyl eugenol, hexyl salicylate, isoeugenol, methyl eugenol, methyl isoeugenol, methyl salicylate, tert butyl cresol, thymol, and vanillin.

5. A fragrance composition according to claim 1, wherein said non-aromatic terpenoid compound is at least one of cedrene, cineole, citral, citronellal, citronellol, cymene, paradihydrolinalool, dihydromycenol, farnesol, geraniol, hexyl cinnamaldehyde, hydroxycitronallol, hydroxycitronellal, isocitral, limonene, linalool, longifolene, menthol, nerol, nerolidiol, phellendrene, terpinene, terpinenol, and tetrahydromycenol.

6. A fragrance composition according to claim 1, further comprising an essential oil, said essential oil containing at least one of said phenolic compound and said non-aromatic terpenoid as a major constituent.

7. A fragrance composition according to claim 6, wherein said essential oil containing said phenolic compound is at least one of anise oil, bay oil terpineless, clove bud, clove leaf, clove oil, clove stem, origanum oil, Peru balsam, pimento oil, and thyme oil.

8. A fragrance composition according to claim 6, wherein said essential oil containing said non-aromatic terpenoid is at least one of buchu oil, caraway oil, carrot seed, cedar leaf, citronella oil, citrus oil, copaiba oil, geranium oil, gergamot, lavender oil, mint oil, orange oil, parsley oil, patchouly oil, pine oil, rosemary oil, sage oil, tagette oil, and ylang ylang.

9. A fragrance composition according to claim 1, further comprising a surfactant, whereby said fragrance composition is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry detergent, deodorant, antiperspirant, bleach, air care products, and a fabric softener.

10. A fragrance composition having antimicrobial activity, comprising:

between 3 and 20% of a phenolic compound; and between 20 and 80% of a non-aromatic terpinoid;

wherein said fragrance composition has an Odor Intensity Index of between 110 and 130, and said fragrance composition has an Odor Evaluation Acceptability Index of greater than 50, and said fragrance composition satisfies at least two of the following four criteria a: said fragrance composition achieves a Minimal Inhibitory Concentration (MIC) in media at or below normal use concentration within two days;

b: said fragrance composition reduces the microbial number by at least 1.5 log cfu/ml within 5 minutes at ambient temperature at or below normal use concentration;

c: said fragrance composition at normal use concentration reduces the microbial number by at least 1.5 log cfu/ml within 5 minutes at product use temperature;

d: said fragrance composition at normal use concentration reduces or inhibits microbial growth.

11. A fragrance composition according to claim 10, wherein said fragrance composition has an Odor Evaluation Acceptability Index of greater than 65.

12. A fragrance composition according to claim 10, wherein said fragrance composition is a member selected from the group consisting of AMPAT-A, AMPAT-B, and AMPAT-C, wherein:

AMPAT-A is a composition containing 4.0 wt. percent citral, 1.5 wt. percent citronellyl nitrile 1, 5.0 wt. percent clove leaf oil, 14.05 wt. percent citrustone 1, 6.0 wt. percent geraniol, 6.0 wt. percent grapefruit oil terpenes, 3.25 wt. percent lime oil terpenes, 7.7 wt. percent linalool, 19.0 wt. percent orange oil terpenes white, 1.0 wt. percent suzaral, 20.0 wt. percent terpinolene 20, 5.0 wt. percent TH myrcenol, and 7.5 wt. percent thymol;

AMPAT-B is a composition containing 3.9 wt. percent eugenol, 8.6 wt. percent thymol, 15.1 wt. percent DH myrcenol, 11.35 wt. percent marine note A, 1.6 wt. percent citral, 8.6 wt. percent geraniol pure, 11.5 wt. percent grapefruit oil terpenes, 7.8 wt. percent cedarwood oil texas white, 0.8 wt. percent linalool, 0.8 wt. percent clove leaf oil, 9.4 wt. percent terpinolene 20, 3.9 wt. percent TH myrcenol, 0.7 wt. percent musk T, 12.0 wt. percent bergamot sub GL berg, 1.9 wt. percent suzaral 0.15 wt. percent oranta, L, super, and 1.9 wt. percent lavandin grosso;

AMPAT-C is a composition containing 1.5 wt. percent amyl salisylate. 4.0 wt. percent bergamot sub GL berg, 1.5 wt. percent cedarwood oil texas white, 3.0 wt. percent cinnaldehyde, 6.5 wt. percent clove leaf oil, 15.0 wt. percent DH myrcenol, 3.0 wt. percent geraniol intermediate 60, 9.6 wt. percent herbal tone F, 3.5 wt. percent hexyl cinnamaldehyde, 9.0 wt. percent hexyl salisylate, 2.0 wt. percent lavandin grosso, 3.5 wt. percent muguet sub GL mugu, 1.5 wt. percent olibanum re "T" @ 50% DPG, 5.0 wt. percent orange oil pera brazil, 1.25 wt. percent patchouly oil deironized, 1.65 wt. percent phellandrene, alpha, 7.0 wt. percent terpinolene 20, 10.0 wt. percent thymol, 1.5 wt. percent verdox, and 10.0 wt. percent vertenex.

13. A fragrance composition according to claim 10, wherein said phenolic compound is at least one of amyl salicylate, carvacrol, dihydroeugenol, eugenol, hexyl eugenol, hexyl salicylate, isoeugenol, methyl eugenol, methyl isoeugenol, methyl salicylate, tert butyl cresol, thymol, and vanillin.

14. A fragrance composition according to claim 10, wherein said non-aromatic terpenoid compound is at least one of cedrene, cineole, citral, citronellal, citronellol, cymene, paradihydrolinalool, dihydromycenol, farnesol, geraniol, hexyl cinnamaldehyde, hydroxycitronallol, hydroxycitronellal, isocitral, limonene, linalool, longifolene, menthol, nerol, nerolidiol, phellendrene, terpinene, terpinenol, and tetrahydromycenol.

15. A fragrance composition according to claim 10, further comprising an essential oil, said essential oil containing at least one of said phenolic compound and said non-aromatic terpenoid as a major constituent.

16. A fragrance composition according to claim 15, wherein said essential oil containing said phenolic compound is at least one of anise oil, bay oil terpineless, clove bud, clove leaf, clove oil, clove stem, origanum oil, Peru balsam, pimento oil, and thyme oil.

17. A fragrance composition according to claim 15, wherein said essential oil containing said non-aromatic terpenoid is at least one of buchu oil, caraway oil, carrot seed, cedar leaf, citronella oil, citrus oil, copaiba oil, geranium oil, bergamot, lavender oil, mint oil, orange oil, parsley oil, patchouly oil, pine oil, rosemary oil, sage oil, tagette oil, and ylang ylang.

18. A fragrance composition according to claim 10, further comprising a surfactant, whereby said fragrance composition is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry detergent, deodorant, antiperspirant, bleach, air care products, and a fabric softener.

* * * * *